United States Patent [19]

Pande et al.

[11] Patent Number: 5,075,213
[45] Date of Patent: Dec. 24, 1991

[54] METHOD FOR DETECTION AND PREVENTION OF HUMAN CYTOMEGALOVIRUS INFECTION

[75] Inventors: Hema Pande, Arcadia; Arthur D. Riggs, La Verne; John A. Zaia, Arcadia, all of Calif.

[73] Assignee: City of Hope, Duarte, Calif.

[21] Appl. No.: 540,876

[22] Filed: Jun. 20, 1990

Related U.S. Application Data

[63] Continuation of Ser. No. 885,386, Jul. 16, 1986, abandoned, which is a continuation of Ser. No. 635,368, Jul. 27, 1984, abandoned.

[51] Int. Cl.$^5$ .......................... C12Q 1/70; C12Q 1/68
[52] U.S. Cl. .......................................... 435/5; 435/6; 435/91; 435/172.3; 435/803; 536/27; 436/63; 436/94; 436/501; 436/504; 935/2; 935/10; 935/77; 935/78
[58] Field of Search ...................... 435/5, 6, 91, 172.3, 435/803; 424/1.1; 436/63, 94, 501, 504, 811; 935/2, 10, 11, 12, 77, 78, 8; 536/27

[56] References Cited

U.S. PATENT DOCUMENTS

4,358,535 11/1982 Falkow et al. ................... 435/35 X
4,762,780 8/1988 Spector et al. ................... 935/78 X

OTHER PUBLICATIONS

Nowak, B. et al., Virology 134 (Apr. 1984), 91–102.
Rüger, B. et al., J. Virology 61 (Feb. 1987), 446–453.
Irmiere, A. et al., Virology 130 (Oct. 1983), 118–133.
Pande, H. et al., Proc. Nat'l Acad Sci. USA, vol. 81, No. 15, 1984, pp. 4965–4969.
Clark, B. R. et al., J. Virology, vol. 49, No. 1, 1984, pp. 279–282.
Stinski, M. F. et al., J. Virology, vol. 46, No. 1, 1983, pp. 1–14.
Gelmann, E. P. et al., Proc. Nat'l Acad. Sci. USA, vol. 80, 1983, pp. 5107–5111.
Fleckenstein, B. et al., Gene, vol. 18, 1982, pp. 39–46.
Tamashiro, J. C. et al., J. Virology, vol. 42, No. 2, 1982, pp. 547–557.
Spector, S. A., The Lancet, Feb. 19, 1983, pp. 378–380.

Primary Examiner—Christine Nucker
Assistant Examiner—Laurie Scheinek
Attorney, Agent, or Firm—Edward S. Irons

[57] ABSTRACT

A DNA probe has been isolated which is capable of hybridizing to an oligonucleotide sequence coding for a polypeptide from a major 64 Kilodalton protein of human cytomegalovirus (HCMVgp64). The probe has a sequence of at least seventeen (17) to as many as seven hundred twenty-one 721) nucleotides. The probe may be labelled as by radioactivity. The probe has been used to screen DNA fragments constituting a subgenomic library of human cytomegalovirus DNA to obtain DNA fragments coding for the major late protein of human cytomegalovirus. The DNA fragments coding for the major late protein of human cytomegalovirus (HCMVgp64) may be hybridized to DNA fragments of HCMV DNA from an individual having human cytomegalovirus infection. The viral DNA can be used as whole HCMV DNA or as fragments formed by digesting the human cytomegalovirus DNA with a restriction endonuclease such as one of the restriction endonucleases EcoRI, BamHI, XbaI, HindIII and PrtI. During the screening of clinical specimens, the DNA fragment coding for HCMVgp64 of human cytomegalovirus hybridizes to whole HCMV DNA or to a particular one of the DNA fragments produced by digesting the human cytomegalovirus DNA with the restriction endonucleases. As a resuslt of such hybridization, the identity of human cytomegalovirus may be established. The particular DNA fragment may have a map location of approximately 0.50 to 0.51 units in the human cytomegalovirus (strain Towne) genome. It may have a sequence of about 721 nucleotides. The major late protein of human cytomegalovirus (HCMVgp64) also reacts with T-lymphocytes of an individual after natural infection of that individual with human cytomegalovirus. Thus, the HCMVgp64 protein may be used as a vaccine to prevent HCMV infection.

7 Claims, 4 Drawing Sheets

AMINO ACID SEQUENCE    Tyr-Gln-Glu-Phe-Phe-Trp-Asp

POSSIBLE CODONS    5' UA$_C^U$ CA$_G^A$ GA$_G^A$ UU$_C^U$ UU$_C^U$ UGG GA$_U^C$ 3'

HCMV PROBE 1    5'    CA$_G^A$ GA$_G^A$ TT$_C^T$ TT$_C^T$ TGG GA 3'

HCMV PROBE 2    5' TA$_C^T$ CA$_G^A$ GA$_G^A$ TT$_C^T$ TT$_C^T$ TGG GA 3'

```
Asn Leu Val Pro Met Val Ala Thr Val Gln Gly Gln Asn
AAC CTG GTG CCC ATG GTG GCT ACG GTT CAG GGT CAG AAT

┌─────────────── T-14 ──────────────────
Leu Lys │Tyr Gln Glu Phe Phe Trp Asp Ala Asn Asp Ile
CTG AAG  TAC CAG GAG TTC TTC TGG GAC GCC AAC GAC ATC

─────────┐┌──────────── T-12 ─────────────────
Tyr Arg │ Ile Phe Ala Glu Leu Glu Gly Val Trp Gln
TAC CGC   ATC TTC GCC GAA TTG GAA GGC GTA TGG CAG

─────────────────────┐
Pro Ala Ala Gln Pro Lys│
CCC GCT GCG CAA CCC AAA
```

Fig. 2

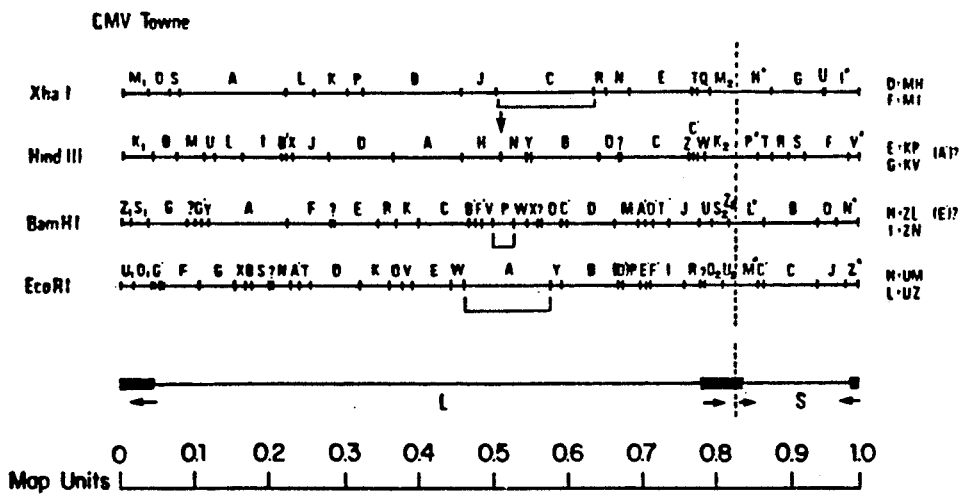

NUCLEOTIDE SEQUENCE OF HCMV-gp64 GENE FRAGMENT

```
  1   GAT CGG ACT CCG ACG AGG AAC TCG TAA CCA   30
 31   CCG AGC GCA AGA CGC CCC GCG TTA CCG GCG   60
 61   GCG GCG CAT GGC GGG CGT CCA CTT CCG CGG   90
 91   GCC GCA AAC GCA AAT CAG CAT CCT CGG CGA  120
121   CGG CGT GCA CGG CGG GCG TTA TGA CAC GCG  150
151   GCC GCC TTA AGG CCG AGT CCA CCG TCG CGC  180
181   CCG AAG AGG ACA CCG ACG AGG ATT CCG ACA  210
211   ACG AAA TCC ACA ATC CGG CCG TGT TCA CCT  240
241   GGC CGC CCT GGC AGG CCG GCA TCC TGG CCC  270
271   GCA ACC TGG TGC CCA TGG TGG CTA CGG TTC  300
301   AGG GTC AGA ATC TGA AGT ACC AGG AGT TCT  330
331   TCT GGG ACG CCA ACG ACA TCT ACC GCA TCT  360
361   TCG CCG AAT TGG AAG GCG TAT GGC AGC CCG  390
391   CTG CGC AAC CCA AAC GTC GCC GCC ACC GGC  420
421   ARG ACG CCT TGC CCG GGC CAT GCA TTC GCC  450
451   TCG ACG CCC AAA AAG CAC CGA GGT TGA GCC  480
481   ACC CGC CGC GCA CGC TTA GGA CGA CTC TAT  510
511   AAA AAC CCA CGT CCA CTC AGA CAC GCG ACT  540
541   TTT GGC CGC CAC ACC TGT CGC CGC TGC TAT  570
571   ATT TGC GAC AGT TGC CGG AAC CCT TCC CGA  600
601   CCT CCC ACG AAG ACC CGT TCA CCT TTG CGC  630
631   ATC CCC TGA CCC CCC CCC TCA TCC CGC CTT  660
661   CGC GAT GTC TCA GGC ATC GTC CTC GCC CGG  690
691   TGA GGG ACC CTC GTC GGA AGC GGC CGC GAT  720
721   C                                        721
```

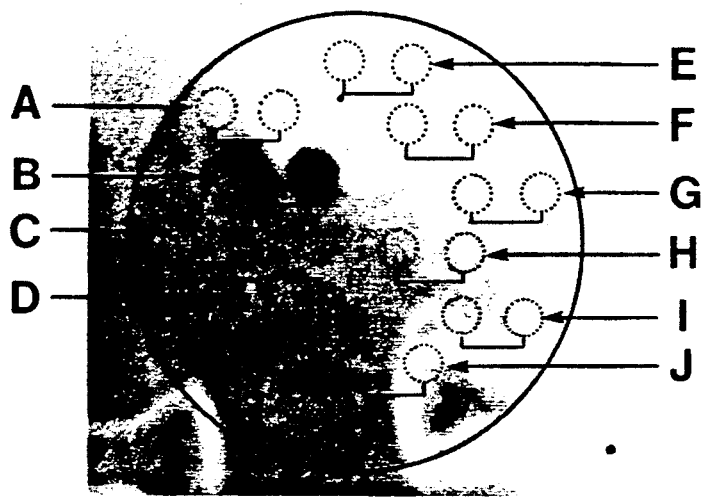

FIG. 6

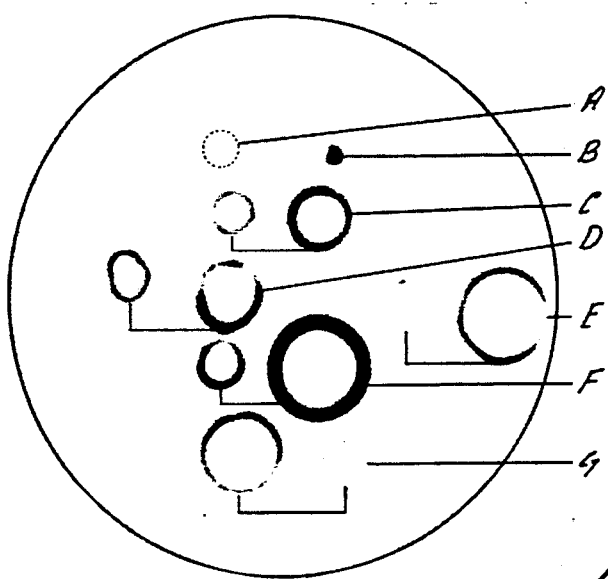

FIG. 7

DOT BLOT ANALYSIS OF WILD ISOLATES. ANALYSIS WAS PERFORMED USING INFECTED CELL LYSATE FROM WILD ISOLATES UNDER THE CONDITIONS DESCRIBED IN FIG. 7. THE AUTORADIOGRAM SHOWS HYBRIDIZATION OF $^{32}P$-LABELED CLONED HCMV-gp64 GENE FRAGMENT TO ALL THE WILD ISOLATES.

A - UNINFECTED CELLS (CONTROL)
B - HCMV (TOWNE)
C, E & G - GRANULOCYTE CULTURE OF PATIENTS AFTER BONE MARROW TRANSPLANTATION
D - LUNG CULTURE OF A PATIENT WITH HCMV ASSOCIATED PNEUMONIA
F - GRANULOCYTA CULTURE OF A PATIENT WITH ACUTE IMMUNODEFICIENCY SYNDROME (AIDS)

METHOD FOR DETECTION AND PREVENTION OF HUMAN CYTOMEGALOVIRUS INFECTION

This is a continuation of Ser. No. 885,386, filed 7/16/86, now abandoned, which is a continuation of Ser. No. 635,368, filed 7/27/84, now abandoned.

This invention relates to methods of diagnosing and preventing human cytomegalovirus infection. It also relates to probes used in diagnosing human cytomegalovirus and to medicines such as vaccines for preventing human cytomegalovirus.

Human cytomegalovirus is a member of the herpes virus group and is a relatively common form of disease. For example, approximately ten percent (10%) of all newborn infants carry human cytomegalovirus. Some of these newborn infants suffer congenital birth defects. Other newborn infants carry cytomegalovirus for some time before they actually show symptoms of the disease. People infected with the disease often suffer impairment of some of their vital organs, including the salivary glands, brain, kidney, liver and lungs, as a result of the effects of the disease. Furthermore, human cytomegalovirus is associated with a wide spectrum of classical syndromes including mononucleosis and interstitial pneumonia. Human cytomegalovirus also has an oncogenic potential and a possible association with certain types of malignancy including Karposi's sarcoma.

Since human cytomegalovirus is relatively common in people, a considerable effort has been made to isolate the disease and to diagnose the disease in patients. Attempts have also been made to prepare a medicine, such as a vaccine, which can be administered to a patient to prevent the disease. In spite of such efforts, no satisfactory method has been developed to isolate, diagnose or treat the disease.

This invention relates to methods of using DNA fragments coding for the a major late 64 Kilodalton protein of human cytomegalovirus (HCMVgp64) to diagnose and prevent the disease. The invention also relates to probes formed from DNA fragments coding for this 64K protein of human cytomegalovirus for use in diagnosing cytomegalovirus in human patients. The invention also relates to vaccines formed from matrix proteins such as HCMVgp64 of human cytomegalovirus for use in preventing the disease. The probes and vaccines can be manufactured simply and reliably and can be applied by technicians to patients to obtain reliable results.

In one embodiment of the invention, a probe is capable of hybridizing to a gene fragment coding for an amino acid sequence of HCMVgp64 protein of human cytomegalovirus. The probe has a sequence of at least seventeen (17) to seven hundred twenty-one (721) nucleotides. The probe may be labelled as by radioactivity. The probe is used to screen DNA fragments constituting a subgenomic library of human cytomegalovirus DNA to obtain DNA fragments coding for the HCMVgp64 of human cytomegalovirus.

The DNA fragments coding for the HCMVgp64 of human cytomegalovirus may be hybridized to whole DNA or to DNA fragments of the DNA of an individual having human cytomegalovirus. The DNA fragments may be formed by digesting the human cytomegalovirus DNA with a restriction endonuclease such as one of the restriction endonucleases EcoRI, BamHI, XbaI, HindIII and PstI. During the "dot-blot" screening procedure, the DNA fragments coding for the HCMVgp64 protein of human cytomegalovirus hybridizes to the DNA of HCMV. As a result of such hybridization, the identity of human cytomegalovirus may be established. This particular DNA fragment may have a map location of approximately 0.50 to 0.51 units in the human cytomegalovirus genome. It may have a sequence of about seven hundred twenty-one (721) nucleotides.

The major late protein of human cytomegalovirus (HCMVgp64) also reacts with T-lymphocytes in an individual after natural infection of that individual with human cytomegalovirus. Thus, the HCMVgp64 protein may be used as a vaccine to treat patients having human cytomegalovirus.

In the drawings:

FIG. 2 is a schematic drawing of the sequence of nucleotides and the sequence of the amino acids of a gene fragment coding for the matrix protein, such as a 64K glycoprotein, of human cytomegalovirus;

FIG. 3A is a representation of the DNA fragments obtained by digesting the cytomegalovirus DNA with different restriction endonucleases and transferring the DNA fragments to nitrocellulose;

Figures 1, 3:
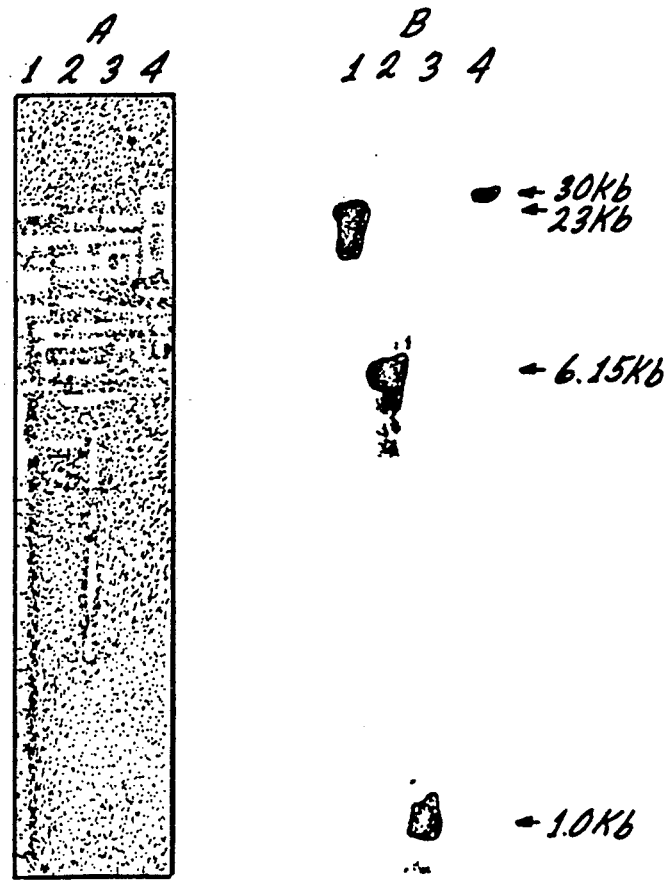
FIG. 1 is a schematic drawing illustrating the sequence of nucleotides in oligonucleotide probes used in isolating and characterizing a genomic clone containing the gene fragment coding for an amino acid sequence of a tryptic peptide of a matrix protein, such as a 64K dalton glycoprotein, which is the major late antigen of human cytomegalovirus.

FIG. 3B is a representation of the results of hybridizing the DNA fragments of FIG. 3A with a labelled, purified and cloned DNA fragment having a sequence of seven hundred twenty-one (721) base pairs; and FIG. 4 is a representation of the mapping of the DNA fragments obtained by digesting the DNA of human cytomegalovirus with the different restriction endonucleases and particularly illustrates the relative location of a particular one of the DNA fragments obtained from such digestion.

FIG. 5 is a table indicating the nucleotide sequence found to exist for a particular gene fragment of human cytomegalovirus; and FIG. 6 is a dot-blot indicating the detection of human cytomegalovirus and the non-detection of other types of herpes viruses.

FIG. 7 is a dot blot indicating the detection of human cytomegalovirus from chemical specimens.

The human cytomegalovirus (HCMV) genome is a linear double-stranded molecule with an approximate size of 240 kilobase pair (kb). The cytomegalovirus DNA consists of a long region and a short region of unique nucleotide sequences which are bounded by inverted repeat regions. Human cytomegalovirus specifies more than 50 unique infected-cell polypeptides with molecular weights ranging from 200 K to 10 k daltons. Of these, a matrix protein of human cytomegalovirus, such as a major structural glycoprotein having an Mr (relative mass) of approximately 64–66 K dalton (HCMVgp64), is present in high abundance during the late stages of human cytomegalovirus infection and is an important antigenic component in serologic tests for human cytomegalovirus. An antibody to the matrix protein of human cytomegalovirus (HCMVgp64) appears after natural infection in both adults and children. HCMVgp64 constitutes a 64K dalton glycoprotein which is the major late synthesis of human cytomegalovirus. A monoclonal antibody specific for this viral protein neutralizes virus infectivity and binds to the plasma membrane of infected cells.

To further an understanding of the precise role of the matrix protein of human cytomegalovirus, such as the 64K dalton glycoprotein (HCMVgp64), in natural human cytomegalovirus infection, applicants attempted to clone the gene coding for this structural protein. Although this polypeptide has been purified from the virions plus dense bodies (HCMV-db) of HCMV, no one has previously identified the portion of the cytomegalovirus DNA coding for this protein.

This invention describes the cloning of a gene fragment coding for a matrix protein of human cytomegalovirus, such as the 64K dalton glycoprotein (HCMVgp64), by means of oligonucleotide probing. Since none of the structural polypeptides of HCMV have been previously mapped, a significant aspect of this invention is the physical mapping of the coding sequences of the matrix protein of human cytomegalovirus HCMVgp64. As will be seen, all of this is used to diagnose human cytomegalovirus in patients and to provide a vaccine for immunizing patients.

MATERIALS AND METHODS

Growth of HCMV. Human cytomegalovirus (HCMV) (Towne strain) was obtained from S. Starr, Philadelphia, Pa., and grown in human foreskin fibroblasts. The growth medium consisted of Dulbecco's modified Eagle medium, supplemented with 10% fetal bovine serum. This medium was maintained in a 10% $CO_2$/90% air atmosphere at 36° C. Fibroblast monolayer cultures were grown in 485 $cm^2$ roller bottles and inoculated with cell-free virus using a multiplicity of infection of 0.1–0.2. Extracellular virus was harvested and virions plus dense bodies (HCMV-db) were prepared as described by B. R. Clark, J. A. Zaia, L. Balce-Directo and Y. P. Ting in 1984 in 49 Journal of Virology 279–282.

Isolation, trypsin digestion and microsequence analysis of HCMVgp64. HCMVgp64 (the 64K dalton glycoprotein) was purified from HCMV-db by reverse phase high performance liquid chromatography as described in 1984 in an article in 49 Journal of Virology 279–282. (Although reference may be made in this application to HCMVgp64, it will be appreciated that this may be considered broadly to be a matrix protein of human cytomegalovirus). Trypsin digestion and separation of tryptic peptides were obtained as specified in 1984 in the article in 49 Journal of Virology 279–282. Amino acid analysis of tryptic peptides was performed on a Beckman 121 MB amino acid analyzer according to the procedures described by U. Del Valle and J. E. Shively in 1979 in 96 Analytical Biochemistry 77–83. Amino terminal sequence analysis of the tryptic peptides was performed by using microsequencing techniques by automated Edman degradation on a modified Beckman 890C sequencer by the method of Shively as described in 1981 in 79 Methods in Enzymology 31–48.

Synthesis of mixed oligodeoxynucleotides. Mixed oligonucleotides seventeen (17) bases and twenty (20) bases long were synthesized by a solid phase phosphotriester approach using protected dinucleotides as described by Z. K. Tan, F. Ikuta, T. Huang, A. Dugaiczk and K. Itakura in 1982 in 47 Cold Spring Harbor Symposium of Quantitative Biology at pages 387–391. The synthetic oligonucleotides seventeen (17) bases and twenty (20) bases long were provided with overlapping relationships as shown in FIG. 1 where the oligonucleotides are designated as HCMV probe 1 and HCMV probe 2. The nucleotide sequences of these probes were based upon the partial amino acid sequence of the matrix protein of human cytomegalovirus (designated in this application as HCMVgp64).

A heptapeptide sequence derived from a tryptic fragment of the matrix protein of human cytomegalovirus (HCMVgp64) was selected for the design of two (2) sets of oligonucleotide mixtures containing all of the possible coding sequences as shown in FIG. 1. Both probes were synthesized in one main synthesis. The first set (designated as HCMV probe 1) was derived from the hexapeptide sequence Gln-Glu-Phe-Phe-Trp-Asp and was synthesized as a mixture of sixteen (16) different heptanucleotides. This mixture of sixteen (16) different oligonucleotides resulted from the variations possible in the third position of each amino acid codon, as may be seen in FIG. 1 from the two indications above each other in the third position for each amino acid sequence.

At the completion of the synthesis of HCMV probe 1, the resin was split and half of it was used for the synthesis of the second probe. The second probe (HCMV probe 2) was based on a heptapeptide sequence derived from the hexapeptide discussed above but containing an additional tyrosine at the $NH_2$ terminus as shown in FIG. 1. This second set of oligonucleotides was synthesized as a mixture of thirty-two (32) different eicosanucleotides. It involved two (2) additional couplings to the second half of the resin.

The oligonucleotides were purified by high performance liquid chromatography on a reverse phase column (Waters Associates $\mu$-Bondapak C-18). Labeling of the purified oligodeoxynucleotides at the 5' end was performed by using T4 polynucleotide kinase and [$\gamma^{32}p$] ATP. The radioactively labeled oligonucleotides were purified on Whatman DE-52 DEAE-cellulose columns as described by R. B. Wallace, M. Schold, M. J. Johnson, P. Dembed and K. Itakura in 1981 in 9 Nucleic Acids Research 3647–3656. After filtration (0.2-$\mu$m-pore Nalgene filters), the probes were used directly for hybridization at a concentration of 0.2 ng/ml per species of probe (about $10^7$) total cpm.

Construction of recombinant plasmids. HCMV DNA was isolated according to the methods described by J. M. Demarchi in 1981 in 114 Virology 23–28 and by M. F. Stinski, E. S. Mocarski and D. R. Thompson in 1979 in 31 Journal of Virology 231–239. The viral DNA was released from purified virions by treatment with 2% sodium lauryl sarkosinate which was pretreated with 150 $\mu$/ml proteinase K. After incubation at room temperature for thirty (30) minutes, the mixture was extracted with equal volumes of phenol and chloroform-isoamyl alcohol (24:1) by gentle shaking on a platform shaker. The DNA was precipitated from the aqueous layer with 95% ETOH.

Plasmid pBR327 was used as a cloning vector. The subgenomic fragments of HCMV DNA generated by digestion with restriction endonuclease Sau3A were ligated with BamHI cut plasmid pBR327 using T4 ligase. The recombinant plasmid was used to transform E. coli strain LSI, a lac+ derivative of RRI (pro, leu, thi, rpsL20, hsdR, hsdM) by the procedure described by T. Maniatis, E. F. Fritsch and J. Sambrook in 1982 in Molecular Cloning: a Laboratory Manual (Cold Spring Harbor Laboratory, Cold Spring Harbor, N.Y.) at pages 254–255. Clones were selected on LB agar plate containing 20 $\mu$g/ml ampicillin.

Screening of HCMV library. Recombinant bacterial clones were screened on Whatman 541 filter papers, amplified with chloramphenicol (250 μg/ml) and prepared for hybridization as described by J. P. Gergen, R. H. Stern and P. C. Wensink in 1979 in 7 Nucleic Acids Research 2115-2136. The filters were prehybridized in 6×SET (1×SET=0.15 M Nacl/0.001 M EDTA/0.015 M Tris-HCl pH 7.5) containing 100 μg/ml sonicated salmon sperm DNA and 0.5% Nonidet P-40. Hybridization to the probe was performed at room temperature in the same buffer. Filters were washed first with 6×SSC (1×XSSC=0.15 M Nacl, 0.015 M sodium citrate, pH 7.2) at room temperature. Three (3) high stringency washes were performed at 43° in the same buffer and then the filters were exposed to x-ray film.

Hybridization of probes to plasmid DNA. Plasmid DNA was prepared according to an article published by D. Ish-Horowitz and J. D. Burke in 1981 in 9 Nucleic Acids Research 2989-2998. The $^{32}p$-labeled probes were hybridized to restriction enzyme-digested plasmid DNA on dried agarose gel at room temperature for approximately 16-18 hours. The buffers used for hybridization and washes were the same as those used for colony hybridization.

Of the approximately 15,000 DNA fragments screened by hybridization to $^{32}p$-labelled HCMV probe 1, two (2) strongly hybridizing colonies were identified. When HCMV probe 2 was used for screening, positive hybridization was observed in the same two (2) colonies. The selection procedure included hybridization with probes at increasing temperatures in which the most stringent conditions approximated the predicted Td (dissociation temperature).

Plasmid DNA was prepared and inserts were analyzed by restriction enzyme mapping. The PstI digested recombinant plasmid DNA in the two (2) positive colonies was compared to PstI digested plasmid pBR327 DNA by electrophoresis on agarose gel. This comparison showed an insert of approximately 2.3 kb as the sequence of nucleotides in the DNA fragments in the two (2) positive colonies. When the recombinant plasmid DNA was digested with restriction enzyme Sau3A and compared with Sau3A digested plasmid pBR327 DNA, two additional fragments, an seven hundred twenty-one (721) bp and a fifteen hundred (1500) bp, were observed for both positive colonies. Of these two fragments, only the seven hundred twenty-one (721) bp fragment hybridized to the $^{32}p$-labeled synthetic probes on nitrocellulose filters by the Southern hybridization method (FIG. 3).

DNA sequence analysis. DNA restriction fragments were cloned into phage cloning vector M13 mp8 and single-stranded phage DNA was isolated as described by J. Messing and J. Vieira in an article published in 1982 in 19 Gene 269-276. Nucleotide sequence analysis was performed by a method using synthetic oligonucleotide primers. This method is described in an article published by F. Sanger, S. Nicklen and A. R. Coulsen in 1977 in 74 Proceedings of the National Academy of Science 5463-5467. Subfragments of the seven hundred twenty-one (721) bp insert were generated by using restriction endonucleases HpaII and SmaI and subjected to nucleotide sequence analysis after subcloning into bacterio- phage M13 mp8 and mp9 respectively.

FIG. 2 shows the combined nucleotide sequence and the deduced amino acid sequences of the most relevant portion of the cloned insert. The tryptic mapping of the matrix protein of human cytomegalovirus (glycoprotein HCMVgp64) has been described in the article by Clark, Zaia, Balce-Directo and Ting specified above. Approximately 3 nanomoles of the HPLC purified matrix protein of human cytomegalovirus (HCMVgp64) were used for these studies and the recovery of tryptic peptides was greater than 90%. The HPLC purified tryptic peptides were arbitrarily numbered from T-1 to T-14 and subjected to amino acid composition analysis. On the basis of the amino acid composition, applicants selected two tryptic peptides T-12 and T-14 (both shown in FIG. 2) having respective retention times of 55.9 and 59.4 minutes, and applicants determined their amino acid sequences. These sequences were then compared with the amino acid sequences predicted from the nucleotide sequences of the cloned DNA. The predicted amino acid sequences were in total agreement with the sequences of the tryptic peptides T-12 and T-14 at the positions shown in FIG. 2.

In FIG. 2, the nucleotide sequences showing a perfect match with the probe sequence are underlined. Certain regions are indicated by bracketed lines. These are the regions where the predicted amino acid sequences are identical to the amino acid sequences of the two tryptic peptides. These are designated in FIG. 2, and discussed above, as T-12 and T-14.

Southern blot analysis. HCMV (Towne) DNA was digested to completion using restriction enzymes EcoRI, BamHI, HindIII and XbaI and by double digestion using BamHI and HindIII. The restriction digests were electrophoresed on agarose gels, stained with ethidium bromide, and blotted onto nitrocellulose. The cloned HCMV insert (721 bp) was nick translated with [$\alpha$-$^{32}p$] dCTP (800 ci/m mol) using a nick translation kit (Amersham). Hybridization was conducted in a mixture containing 6×SSC, 1.0 mM EDTA, 5×Denhardt's solution, 0.5% sodium dodecyl sulfate and denatured salmon sperm DNA at 100 g/ml, at 68° for 16-18 hours. Filters were then washed with 0.1×SSC and 0.5% sodium dodecyl sulfate at 68° for 2 hours, dried and exposed to x-ray film as discussed by EM. Southern in 1975 in 98 Journal of Molecular Biology 503-517.

Mapping of the gene coding for the matrix protein of human cytomegalovirus (HCMVgp64). The seven hundred twenty-one (721) bp HCMV insert was gel purified, nick translated and hybridized to HCMV DNA digested with restriction endonucleases EcoRI, BamHI, XbaI, HindIII and a digestion with both the restriction endonucleases BamHI and HindIII.

The restriction fragments were subjected to electrophoresis on 0.7% agarose gels and visualized with an ethidium bromide stain. The results are shown in FIG. 3A. FIG. 3A shows the pattern of DNA fragments generated in the ethidium bromide-stained gel after digestion of HCMV DNA with EcoRI, BamHI, XbaI and HindIII. Columns 1, 2, 3 and 4 in FIG. 3A respectively show the pattern of DNA fragments generated after digestion with the restriction endonucleases EcoRI, BamHI, HindIII and XbaI.

The DNA fragments were then transferred to nitrocellulose by Southern blotting and hybridized to $^{32}p$-labeled purified seven hundred twenty-one (721) bp cloned DNA. The filters were washed sequentially as follows: 1×SSC, 0.1% sodium dodecyl sulfate, for thirty (30) minutes at room temperature and 0.1×XSSC, or 0.5% sodium dodecyl sulfate for two (2) hours at 68° C. After washing, the filters were subjected to autoradiography.

The HCMV restriction fragments showing hybridization to the labeled probe were characterized and are shown in FIG. 3B. Columns 1, 2, 3 and 4 in FIG. 3B respectively show the fragments hybridized to the labeled probe when the fragments were obtained by digestion of the cytomegalovirus DNA with the restriction endonucleases EcoRI, BamHI, HindIII and XbaI.

The HCMV restriction fragments showing hybridization to the labeled probe were characterized. These characterized fragments are shown in FIG. 3B. The slowest moving EcoRI fragment of HCMV in column 1 of FIG. 3B had a size of 23 kb in applicants' gels and hybridized strongly to the cloned fragment. In addition, strong hybridization was observed to a 6.15 kb BamHI fragment as shown in column 2 of FIG. 3B and to a large fragment (approximately 30 kb in size) of the HCMV-XbaI digest as shown in column 4 of FIG. 3B. The HCMV DNA digested with HindIII, and a BamHI/HindIII double digest (data not shown), gave a small fragment approximately 1 kb in size (as shown in column 3 of FIG. 3B) which showed hybridization to the same seven hundred twenty-one (721) bp probe.

Applicants have used the results of the Southern blots, shown in FIG. 3 and discussed in the previous section, to locate the cloned gene fragment coding for the matrix protein, such as HCMVgp64, on the HCMV genome. FIG. 4 illustrates the restriction endonuclease maps for the Towne strain of HCMV. Each of the first four (4) rows of FIG. 4 shows the location for the different DNA fragments when the cytomegalovirus DNA are respectively digested by the restriction endonucleases XbaI, HindIII, BamHI and EcoRI. The last row of FIG. 4 shows mapping units between 0.0 and 1.0 and identifies the location in such mapping units of each of the DNA fragments in the first four rows of FIG. 4.

The different letters in each row in FIG. 4 identify the location of the different DNA fragments in that row. The map locations of the DNA fragment hybridized to the probe after digestion of the cytomegalovirus DNA fragment of seven hundred twenty-one base pairs (721 bp) with the different restriction endonucleases are indicated at A in the fourth row (HCMV EcoRI), at P in the third row (HCMV-BamHI) and at C in the first row HCMV-XbaI) and are shown by bracketed underlines in such rows. More precisely, the map location has been assigned a position between fragments H and N in the second row in FIG. 4B. This position is indicated by an arrow in the second row (HCMV-HindIII) of FIG. 4B.

EXPERIMENTS WITH CLONED DNA a. Detection of Viral Sequences in HCMV Infected Cells by Dot-Blot Hybridization FIG. 5 specifies the nucleotide sequence of a $^{32}p$-labelled nick translated 721 bp Sau3A fragment of the recombinant plasmid. This DNA fragment contains the exact nucleotide sequences as predicted from the amino acid sequence of tryptic peptide of HCMVgp64. This DNA fragment was used as a hybridization probe to analyze by dot-blot analysis the purified DNAs or cell lysates from human foreskin fibroblast cell lines infected with three different HCMV lab strains (Towne, Ad 169 and Davis). In a similar experiment this probe was used to analyze other herpes viruses (FIG. 6), which included two (2) strains of simian CMV (Rhesus and Verret), two (2) strains of VZV (212B and target), two (2) strains of HSV-1 (McIntyre and BK) and two strains of HSV-2 (MS and 186). DNA from uninfected cells was used as negative controls. In this experiment, the labelled cloned 740 bp fragment hybridized specifically only to the DNA of HCMV and showed no hybridization to the DNA from other herpes viruses (FIG. 6). These results indicate that the cloned DNA fragment is specific for HCMV and can be used as a specific probe for detecting HCMV sequences during HCMV infection.

In a similar experiment, the $^{32}p$-labelled 740 bp cloned fragment was also used for analyzing a number of wild isolates of HCMV. Five (5) different wild isolates including three (3) isolates from granulocyte cultures from patients after bone marrow transplantation, one lung tissue isolate from a patient with HCMV associated pneumonia and one isolate from granulocytes of a patient with acquired immunodeficiency syndrome (AIDS) were used. Purified DNA from HCMV (Towne) were used as a positive control and DNA from uninfected cells were used as negative control. Using this technique, all of the five (5) clinical isolates were found to be expressing HCMV DNA (FIG. 7).

b. Identification of HCMV-Infected Cells by in situ-cytohybridization

This technique provides a means of identifying specific cells which are expressing a specific gene. In general, only those cells actively expressing the gene in question will contain enough copies of homologous RNA to hybridize with the radioactively-labelled probe sufficiently to produce a signal detectable by autoradiography. CMV-infected cells were deposited on oxides, fixed, treated with HCE followed by heating at seventy degrees (70°), digested with proteinase K, and dehydrated in graded ethanol. DNA-RNA in situ cytohybridization was conducted overnight at twenty to thirty degrees (20°-°) C. The slides were washed extensively in hybridization buffer and dehydrated in graded ethanol and DNA-RNA hybrids were detected. Using this technique, $^{32}p$-labelled nick translated recombinant plasmid containing the nucleotide sequences coding for HCMVgp64 was able to distinguish, from the uninfected cells, human cell lines which were infected with HCMV.

DISCUSSION

As discussed by M. F. Stinski in 1977 in 23 Journal of Virology 751–767 and by M. W. Wathen and M. F. Stinski in 1982 in 41 Journal of Virology 462–477, HCMV has been shown to undergo regulated phases of transcription and translation, thus giving rise to immediate-early, early and late transcripts. While some of the immediate early (IE) viral proteins may have regulatory functions necessary for efficient transcription, the late transcripts comprise largely the structural polypeptides. Several groups have reported the cloning of restriction fragments of HCMV in plasmid and cosmid vectors. This has provided a basis for constructing cleavage maps and determining the structural organization of the HCMV genome. Furthermore, the transcription pattern of HCMV genome has been investigated at various phases of infection as reported by J. M. Demarchi in 1981 in 114 Virology 23–38 and M. W. Wathen and M. F. Stinski in 1982 in 41 Journal of Virology 462–477.

In order to correlate a defined virion protein with the respective coding sequence, applicants have utilized an approach which is based on protein sequence information. Synthetic oligonucleotides modeled after the amino acid sequences of the matrix protein of human cytomegalovirus, such as HCMVgp64, were utilized for the probing of a library of HCMV subgenomic DNA. Recent advances in protein purification and microsequencing have made this approach quite general, relatively rapid and applicable to many viral proteins.

The use of relatively short probes up to 14 bases has long been known to give frequent false positives in which the clones have only partial nucleotide matches with the probes. The use of either two overlapping probes or a second probe directed against a different site in the protein has been suggested to overcome this problem. Applicants evaluated two oligonucleotide probes seventeen (17) bases and twenty (20) bases in length because applicants were not certain what length (and sequence complexity due to codon degeneracy) would be necessary for optimal screening efficiency. Applicants' results have demonstrated that a mixture of sixteen (16) heptadecanucleotides and a mixture of thirty-two (32) eicosanucleotides are similar in terms of giving strong signal-to-noise ratio in both colony screening and plasmid DNA screening.

By comparing nucleotide sequences with amino acid sequences of tryptic peptides, evidence has been provided that the cloned DNA contains sequences coding for the matrix protein of human cytomegalovirus such as HCMVgp64. The strategy that applicants used to obtain such information is as follows:

Applicants determined amino acid compositions of all the purified tryptic peptides produced from the matrix protein of human cytomegalovirus such as HCMVgp64. Of these peptides, applicants initially selected the sequence T-14 (see FIG. 2) for microsequencing. Analysis of the amino acid sequence of this peptide provided a single sequence through the COOH-terminus and provided information for the design of synthetic probes. The entire amino acid sequence of this peptide was later revealed to have complete agreement with the nucleotide sequence of a portion of the cloned DNA, thus providing evidence that the cloned DNA coded for the matrix protein of human cytomegalovirus such as HCMVgp64.

To further confirm this identity between the amino acid sequence of the peptide and the nucleotide sequence of a portion of the cloned DNA, applicants identified another tryptic peptide T-12 (see FIG. 2), which, on the basis of amino acid composition, corresponded to a region located 3' to the coding sequences of T-14. When subjected to microsequence analysis, this peptide also yielded a unique sequence and showed a perfect match with the amino acid sequence deduced from the nucleotide sequence. Applicants believe that these results provide the first information of the amino acid and gene sequences of the matrix protein of human cytomegalovirus such as HCMVgp64.

Very little has been known in terms of precise map positions of the genes encoding specific HCMV proteins. Stinksi et al have recently identified, in an article published by them in 1983 in 46 Journal of Virology 1-14, the coding region of a 72K dalton immediate-early protein by in vitro translation of mapped mRNA. However, the mapping of the structural proteins of HCMV has not been reported to date. In herpes simplex virus, the use of intertypic recombinants based on ts mutants has permitted the physical mapping of a number of structural polypeptides. This has been disclosed by H. S. Marsden et al in 1978 in 28 Journal of Virology 624-642 and by L. S. Morse et al in 1978 in 26 Journal of Virology 389-410. However, in the case of a slowly replicating virus such as HCMV, such an approach hs not been feasible.

The method for mapping disclosed and claimed in this application utilizes a cloned DNA which contains the nucleotide sequences coding for a defined virion polypeptide. This method is accordingly a relatively direct route to the mapping of specific proteins. Using this approach, applicants have been able to characterize and physically map the coding sequences of the matrix protein of human cytomegalovirus, such as HCMVgp64, in an area of HCMV genome which has been observed not to be homologous to cellular genes.

It has been previously shown by Clark et al in 1984 in 49 Journal of Virology 279-282 that the matrix protein of human cytomegalovirus such as HCMVgp64 contains approximately 2.34% (wt/wt) of galactosamine. The exact function of this protein and a uniform nomenclature have not been established. However, HCMVgp64 appears to be a matrix protein based upon parallel studies with the Colburn strain CMV, a simian virus. This protein is overproduced late in infection, and it forms more than ninety percent (90%) of the protein mass of HCMV dense bodies, which are membrane-bound, DNA-free, protein aggregates. The antigens conventionally used for HCMV serologic testing are rich in the matrix protein of human cytomegalovirus, such as HCMVgp64, and antibody to this protein occurs after natural infection. The role of the matrix protein of human cytomegalovirus, such as HCMVgp64, during natural infection is not known, but it is possible that, if overproduction of this material occurs in vivo, it will have some influence on pathogenesis of HCMV disease.

The cloning of the gene for the matrix protein of human cytomegalovirus, such as HCMVgp64, should make it possible to produce, by chemical synthesis or by expression in prokaryotic or eukaryotic cells, polypeptides containing this sequence and variations of this sequence. The expressed proteins should provide material that will be useful as a laboratory diagnostic reagent.

This has been confirmed by tests which have been performed with a cloned 800 base pair DNA fragment obtained as discussed above. This DNA fragment codes for a portion of the matrix protein of the human cytomegalovirus, such as the 64K dalton glycoprotein. This DNA fragment has been used as a probe for HCMV-specific DNA sequences infection cells. This portion of the genome has not been reported to be homologous to either cellular or onc genes. The eight hundred base pair (800 bp) DNA was $^{32}p$-labeled.

Applicants have used the labeled DNA fragment as a probe in dot blot assays to determine whether the cloned fragment would hybridize to various herpes virus-infected cells and uninfected cells. These herpes virus-infected cells included cells infected with three laboratory strains of human cytomegalovirus (Towne, AD169 and Davis) and with all clinical isolates of human cytomegalovirus. The herpes virus cells also included herpes simplex virus types 1 and 2, varicella, zoster virus and several simian cytomegaloviruses.

In the tests specified in the previous paragraph, hybridization was detected with extracts from cells infected with the three laboratory strains of HCMV (Towne, AD169 and Davis) and with all clinical isolates tested to date. The cloned fragments did not hybridize to extracts from cells infected with herpes simplex virus types 1 and 2, varicella zoster virus, the different simian cytomegalovirus and the uninfected cells. Since the fragment coding for the matrix protein of human cytomegalovirus, such as HCMVgp64, appears to hybridize specifically only with nucleotide sequences found in HCMV-infected cells, this probe can be used to differentiate HCMV from other herpes viruses.

The tests performed to diagnose human cytomegalovirus (HCMV) have advanced through several stages. Initially the effectiveness of the in situ cytohybridization technique was demonstrated on human foreskin fibroblast cells maintained in culture and infected with HCMV in vitro. The results demonstrated the specificity of the probe of the matrix protein of human cytomegalovirus, such as HCMVgp64, to such in vitro infected cells and the lack of specificity of such matrix protein probe to uninfected control cells. Subsequently this technique was shown to be effective on sections of lung tissue taken at autopsy from bone marrow transplant patients who had died from HCMV pneumonia. In other words, the probe hybridized specifically to HCMV-infected lungs.

Applicants have determined that there is a T-lymphocyte reactivity to the matrix protein of human cytomegalovirus (HCMVgp64) following natural infection of an individual with HCMV. This is the first HCMV protein to which T-lymphocyte reactivity has been demonstrated. Because T-lymphocyte immunity appears to be important for recovery from HCMV infection, HCMVgp64 appears to be a candidate vaccine for HCMV.

To confirm the discussions in the previous paragraph, peripheral blood mononuclear leukocytes were separated using Ficoll-hypaque, washed, suspended in RPMI-1640 medium with ten percent (10%) AB+, Rh+ human serum and were then cultured at 37° C. in microtiter plates ($10^5$ cells/well). Different samples of the peripheral blood mononuclear leukocytes were then stimulated with optimal dilutions of individual ones of (a) the matrix protein of human cytomegalovirus (HCMVgp64) such as HCMVgp64, (b) HCMV-infected cell lysate and (c) control cell lysate, and cultures were analyzed for proliferation and for lymphokine production.

The matrix protein of human cytomegalovirus (4 µg/ml) stimulated $H^3$-thymidine in HCMV seropositive donor peripheral blood mononuclear leukocytes but not in seronegative donor peripheral blood mononuclear leukocytes. The peripheral blood mononuclear leukocytes produced the same stimulation with HCMV-infected cell lysate as when the matrix protein of human cytomegalovirus (HCMVgp64) was used. The matrix protein of human cytomegalovirus (HCMVgp64) induced interleukin-2 (IL-2) production, IL-2 receptor expression and interferon production. The additional of antibody to the IL-2 receptor blocked the reactivity of the peripheral blood mononuclear leukocytes to HCMVgp64.

Although this application has been disclosed and illustrated with reference to particular applications, the principles involved are susceptible of numerous other applications which will be apparent to persons skilled in the art. The invention is, therefore, to be limited only as indicated by the scope of the appended claims.

We claim:

1. A probe capable of stable hybridization for use in identifying whether a human patient has human cytomegalovirus, said probe constituting a DNA fragment coding for a matrix protein of human cytomegalovirus and obtained in the late stages of infection with human cytomegalovirus and being obtained from at least a portion of the 64-66K dalton glycoprotein of human cytomegalovirus.

2. A method of identifying the existence of human cytomegalovirus in a human patient, including the steps of:
   (i) forming DNA fragment coding for an amino acid sequence of a tryptic peptide of a 64K-66K glycoprotein which is the major late antigen of human cytomegalovirus,
   (ii) forming a subgenomic library of DNA fragments from human cytomegalovirus DNA,
   (iii) stably hybridizing the coded fragments of step (i) to at least one of the particular DNA fragments in the subgenomic library and human cytomegalovirus DNA, and
   (iv) identifying the stably hybridized pairs in the subgenomic library of DNA fragments by a dot-blot assay.

3. A method of identifying the existence of human cytomegalovirus in a human patient, including the steps of:
   (i) forming a subgenomic library of DNA fragments from the human cytomegalovirus DNA of the human patient,
   (ii) forming a probe constituting a DNA fragment and coding for an amino acid sequence of a tryptic peptide of a 64K-66K dalton glycoprotein which is the major late antigen of human cytomegalovirus and capable of stably hybridizing to a particular one of the DNA fragments from the human cytomegalovirus DNA of the human patient and of stably hybridizing to human cytomegalovirus DNA,
   (iii) stably hybridizing the probe to at least one of the particular one of the DNA fragments in the subgenomic library and of human cytomegalovirus DNA, and
   (iv) identifying the existence of human cytomegalovirus in the human patient by stably such hybridization.

4. A method as set forth in claim 3 wherein the particular one of the DNA fragments has a map location of approximately 0.50 to 0.51 units in the human cytomegalovirus genome (strain Towne).

5. A method as set forth in claim 2 wherein the subgenomic library of the DNA fragments is formed by digesting the DNA of the human cytomegalovirus of the human patient by one of the restriction endonucleases EcoRI, BamHI, XbaI, HindIII and PstI.

6. A method of diagnosing whether a human patient has human cytomegalovirus infection, including the steps of:
   (i) providing human cytomegalovirus DNA from the human patient,
   (ii) forming a probe from a DNA fragment coding for 64K dalton glycoprotein which is the major late antigen of human cytomegalovirus, the probe being capable of stably hybridizing to a particular one of the DNA fragments generated by digesting the human cytomegalovirus DNA of the patient with a particular restriction endonuclease and also being capable of stably hybridizing to the human cytomegalovirus DNA, and (iii) stably hybridizing the probe to at least one of the whole human cytomegalovirus DNA or the particular one of the DNA fragments generated by digesting the cytomegalovirus DNA of the patient with the particular restriction endonuclease.

7. A probe for use in identifying whether a human patient has human cytomegalovirus comprising a DNA fragment coding for a 64K to 66K dalton glycoprotein which is the major late antigen of human cytomegalovirus, said probe having properties of hybridizing stably to whole human cytomegalovirus DNA and to a particular one of the DNA fragments generated by digesting the human cytomegalovirus DNA of the human patient with a restriction endonuclease.

* * * * *

UNITED STATES PATENT AND TRADEMARK OFFICE
CERTIFICATE OF CORRECTION

PATENT NO. : 5,075,213

DATED : December 24, 1991

INVENTOR(S) : Hema Pande, Arthur D. Riggs and John A. Zaia

It is certified that error appears in the above-identified patent and that said Letters Patent is hereby corrected as shown below:

Column 1, after line 7, insert:

--This invention was made with government support under Grant No. CA30206 awarded by the National Institutes of Health. The government has certain rights in the invention.--

Signed and Sealed this

Thirtieth Day of March, 1993

*Attest:*

STEPHEN G. KUNIN

*Attesting Officer*     *Acting Commissioner of Patents and Trademarks*